United States Patent [19]

Madigosky et al.

[11] 4,352,292
[45] Oct. 5, 1982

[54] INSTRUMENT FOR MEASURING DYNAMIC VISCOELASTIC PROPERTIES

[75] Inventors: Walter M. Madigosky; Gilbert F. Lee, both of Silver Spring, Md.

[73] Assignee: The United States of America as represented by the Secretary of the Navy, Washington, D.C.

[21] Appl. No.: 172,585

[22] Filed: Jul. 28, 1980

[51] Int. Cl.³ .................................... G01N 29/00
[52] U.S. Cl. .................................. 73/575; 73/584; 73/574
[58] Field of Search ............... 73/575, 573, 574, 584

[56] References Cited

U.S. PATENT DOCUMENTS

| | | | |
|---|---|---|---|
| 3,176,505 | 4/1965 | Hendrickson | 73/584 |
| 3,550,427 | 12/1970 | Sueyoshi et al. | 73/574 |
| 3,933,032 | 1/1976 | Tschoegl | 73/575 |

*Primary Examiner*—Anthony V. Ciarlante
*Attorney, Agent, or Firm*—R. S. Sciascia; A. L. Branning; W. R. Henderson

[57] ABSTRACT

A method and apparatus for measuring the dynamic material constants of rubber compounds. The rubber compound is tested in strip form by attaching one end of the strip to an electromechanical shaker while the opposite end of the strip is suspended under constant tension. The electromechanical shaker propagates an acoustic wave in the test strip and a piezoelectric transducer positioned at a first point on the test strip measures the mechanical response of the strip for phase and amplitude. The shaker is programmed to step piecewise over the frequency range from 100 Hz to 40 KHz by a frequency synthesizer. The distance between the shaker and the transducer is changed and data is obtained for a second point on the strip. The test values obtained are used to calculate Young's Modulus and the loss factor for the rubber compound.

19 Claims, 11 Drawing Figures

INSTRUMENT FOR MEASURING DYNAMIC VISCOELASTIC PROPERTIES

BACKGROUND OF THE INVENTION

Progressive wave techniques have been used to determine the dynamic material constants of rubber compounds. These techniques commonly use piezoelectric transducers which contact lightly on the surface of a test strip. The strip is excited into oscillation by an electromechanical shaker. One technique is to use two piezoelectric transducers in contact with the test strip. The transducers measure the amplitude and phase differences for a given length of the test strip. In a second technique the strip is excited into oscillation by an electromechanical shaker and a single piezoelectric transducer is moved along the surface of the test strip so that a continuous record is made of the amplitude level and relative phase as a function of distance along the test strip at one frequency. From the record obtained, the attenuation or loss factor is determined and the wavelength is determined between points of equal relative phase along the strip. Since the frequency is known, the propagation velocity can be determined.

The prior art progressive wave techniques are difficult to use since the data is taken by hand at each discrete frequency making the measurements a very time-consuming process. A disadvantage of the first technique is that the responses of the two piezoelectric transducers are not equal and consequently produce large errors in the amplitude and phase measurements. A serious disadvantage of the second technique is that the piezoelectric transducer is not only sensitive to the response of the excited strip but is also sensitive to variations in the surface roughness of the strip which introduces non-systematic errors into the measurements.

SUMMARY OF THE INVENTION

Accordingly, in the present invention there is provided a method and apparatus for measuring the dynamic material constants for rubber compounds. A rubber compound such as nitrile, neoprene or polyurethane is tested to determine the Young's modulus and loss factor. One end of the strip is attached to an electromechanical shaker while the opposite end of the strip is suspended under constant tension. The electromechanical shaker propagates an acoustic wave in the test strip and a piezoelectric transducer positioned at a first point on the strip measures the mechanical response of the strip for relative phase and amplitude.

The shaker is programmed to step piecewise over the frequency range from 100 Hz to 40 KHz by a frequency synthesizer. The source signal from the synthesizer is pre-filtered, to provide a constant output level at the network analyzer, and then amplified by a 20-W power amplifier. The signal from the piezoelectric transducer is amplified and routed to the network analyzer which measures and digitizes the phase angle and amplitude differences between the synthesizer and the transducer. A programmable calculator controls the frequency sweep of the frequency synthesizer and collects and stores the data obtained by the transducer at the first point on the strip.

After the data is accumulated at the first point, the shaker is adjusted relative to the transducer so as to position the transducer at a second point on the strip where a second set of data is obtained over the frequency range. The data obtained at the first and second points is used to calculate the Young's modulus and loss factor at a given frequency for the strip tested.

OBJECTS OF THE INVENTION

It is an object of the present invention to provide apparatus for measuring the viscoelastic properties of rubber compounds.

Another object is to provide a method for measuring the dynamic material constants of rubber compounds.

Yet another object is to provide a method of continuously measuring the viscoelastic properties of rubber compounds over a frequency range.

Still another object is to provide a method of measuring the viscoelastic properties of rubber compounds which minimizes measurement variations due to the surface roughness of the compound.

Another object is to provide an apparatus for reliably and rapidly measuring the dynamic viscoelastic constants of rubber compounds over a complete frequency range.

Other objects, advantages and novel features of the present invention will become apparent from the following detailed description of the invention when considered in conjunction with the drawings.

BRIEF DESCRIPTION OF THE DRAWINGS

A more complete appreciation of the invention and many of the attendant advantages thereof will be readily understood by reference to the following detailed description when considered with the accompanying drawings in which like reference numerals designate like parts throughout the figures and wherein.

DESCRIPTION OF THE PREFERRED EMBODIMENT

Figure 1:
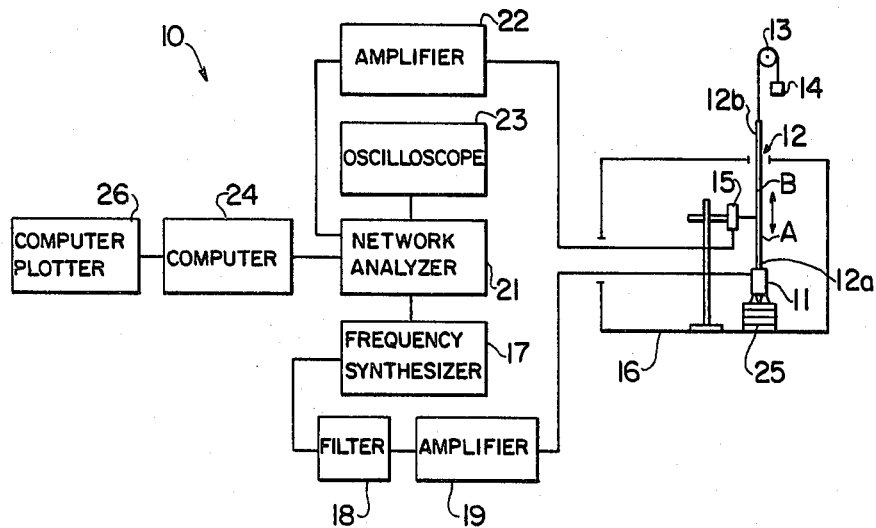
FIG. 1 shows a schematic diagram of the apparatus of the subject invention.

Referring to FIG. 1 there is illustrated in schematic form an instrument 10 for measuring the dynamic material constants of rubber compounds. An electromagnetic shaker 11, such as a Bruel and Kjaer Mini-Shaker type 4810, for example, is used to extensionally drive a test strip 12 composed of the rubber compound to be tested. The rubber strip is 60 cm in length, 0.6 cm in width and 0.3 cm in thickness. The shaker is attached to end 12a of the strip while the opposite end 12b is placed under constant tension by pulley 13 and weight 14. A piezoelectric transducer, such as a Micro-Acoustic 2202 E phonograph cartridge 15 which has good frequency response and tracking capabilities, is positioned adjacent the test strip to measure the mechanical response of the vibrating strip. The electromechanical shaker, rubber strip and cartridge are positioned in a refrigerator oven 16 to enable temperature regulation of the test conditions.

Electromechanical shaker 11 is programmed to step piecewise over the frequency range by a frequency synthesizer 17 such as a Hewlett-Packard 330B, for example. The source signal from the synthesizer is filtered by filter 18 then amplified by a 20 watt power amplifier 19. The filter lowers the source signal level at low frequencies in order to provide a constant output level to network analyzer 21 which can be a Hewlett-Packard 3570A, for example. The signal from cartridge 15 is amplified by amplifier 22 which can be a Tektronix AM 502 differential amplifier, for example. The signal from amplifier 22 is then routed to network analyzer 21 which measures and digitizes the phase angle and amplitude differences between the reference output signal from frequency synthesizer 17 and the measured signal from cartridge 15. The analog and measured signals are displayed on oscilloscope 23.

The acquisition of the data is automated with a mini-computer 24 such as a Hewlett-Packard 9825A calculator, for example. The mini-computer is programmed to initiate and control the frequency sweep of frequency synthesizer 17. Mini-computer 24 also collects and stores the data from the output of network analyzer 21.

Cartridge 15 is positioned at a first point A on test strip 12 which is 1 cm above electromechanical shaker 11, for example. Activation of shaker 11 excites an extensional acoustic wave along test strip 12. The length of test strip 12 is sufficient to prevent generation of a standing wave pattern and the width of the strip is a small fraction of a wavelength such that all portions of the test strip cross section experience similar deformation at the same time. This deformation is associated with Young's modulus.

The extensional sound speed and attenuation are measured as a function of frequency and temperature as controlled by frequency synthesizer 17 and refrigerator oven 16. Measurments are made over a frequency range of 100 Hz–40 KHz. The exact limits of the frequency range are dependent upon the attenuation and wave velocity in the test strip. At high temperature, the loss per centimeter may be very high, thus reducing the high frequency range, whereas at low temperature the loss may be too low to measure at low frequencies.

With cartridge 15 positioned at point A and the shaker activated to sweep through the frequency range, fifty data points are accumulated in less than 10 seconds. Spacers 25, positioned under the shaker, are then removed such that the distance between the cartridge and the top of the shaker is increased to 1.5 to 10 cm and the test strip is repositioned with point B adjacent cartridge 15. A second set of data is collected at point B as the shaker sweeps through the frequency range. The difference in distance between point A and point B is recorded in the mini-computer. Spacers 25 can also be positioned under cartridge 15.

The absolute phase angle and amplitude are determined from the relative phase angle and amplitude differences, respectively, measured at point A and point B for a given frequency. The sound speed and attenuation or Young's modulus and loss factor can be automatically determined by computer 24 and plotted versus frequency on a plotter 26 such as a Hewlett-Packard 9862A calculator plotter, for example.

The sound speed c and attenuation $\alpha$ are expressed in terms of the two measured values phase angle P and amplitude A:

$$c = 360FL/P \text{ cm/s,} \qquad (1)$$

and $$\alpha = (A/L) \text{ dB/cm,} \qquad (2)$$

where F is frequency (Hz), and L (cm) is the length between the initial and final positions of the cartridge, point A and point B, respectively.

The real part of Young's modulus E' is calculated from c and r:

$$E' = \rho c^2(1-r^2)/(1+r^2)^2 \text{ dyn/cm}^2, \qquad (3)$$

where $\rho$ is the density of the rubber strip (g/cm$^3$). The loss factor $\delta$ is defined as the ratio of the imaginary (E'') to real parts and is given by $$\delta = 2r/(1-r^2), \qquad (4)$$

where $$r = \alpha\lambda/[2(8.69)] = 6.59A/P, \qquad (5)$$

and $\lambda$ is the wavelength (cm).

Using the modulus and loss factor data, master curves (complete modulus-frequency and loss factor-frequency behavior at a constant temperature) are constructed by a shifting procedure. This procedure is based on the principle of time-temperatures superposition. The principle states that measurements made over an accessible frequency scale for several temperatures are the same as one measurement made over a large frequency range at one temperature. Applying this principle to the data shown in FIG. 2, we observe that shifting the modulus curve at 17° C. horizontally to the right results in a superposition with the modulus curve at 25.8° C. in the area where the two curves overlap. The new modulus curve at 25.8° C. is extended to higher frequencies and to higher modulus values than previously measured at 25.8° C. Continuing this process, a master curve is generated for both the modulus and loss factor.

The amount of shift, that is required, varies with the temperature. The analytic form of this function is given by the equation which relates the amount of horizontal shift required to superimpose a curve measured at a temperature T onto another curve at a reference temperature $T_o$:

$$\log a_T = -c_1(T-T_o)/(c_2+T-T_o). \qquad (6)$$

The shift factor $a_T$ is equal to the ratio of the shifted frequency F to the reference frequency $F_o$. The constants $c_1$ and $c_2$ are the shift constants which are characteristics of the polymer. In order to evaluate the constants $c_1$ and $c_2$ from the experimental data, the following procedure was used. Rearranging Eq. (6), $$(T-T_o) = -c_1(T-T_o)/\log a_T - c_2 \qquad (7)$$

is obtained, then a plot of $(T-T_o)$ vs $(T-T_o)/\log a_T$ has a slope equal to $-c_1$ and an intercept of $-c_2$.

Figure 8:
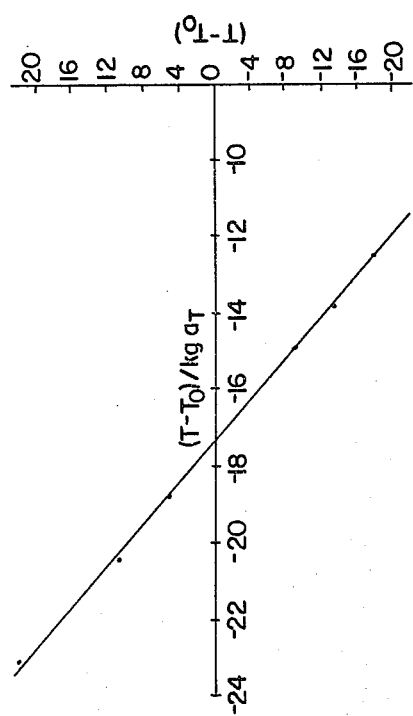
FIG. 8 illustrates a shift plot for neoprene rubber.
Figure 9:
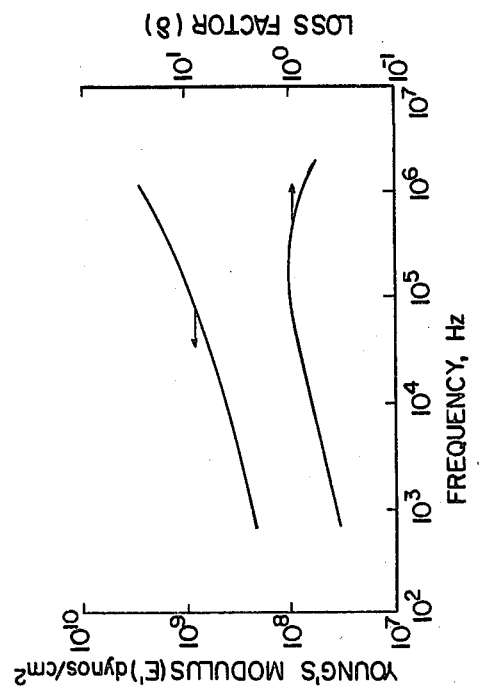
FIGS. 9–11 illustrate master curves for Young's modulus and loss factor for various rubbers.
Figure 10:
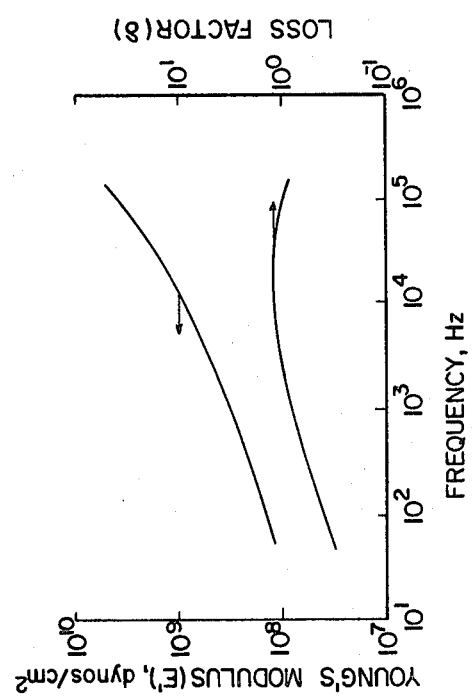
Figure 11:
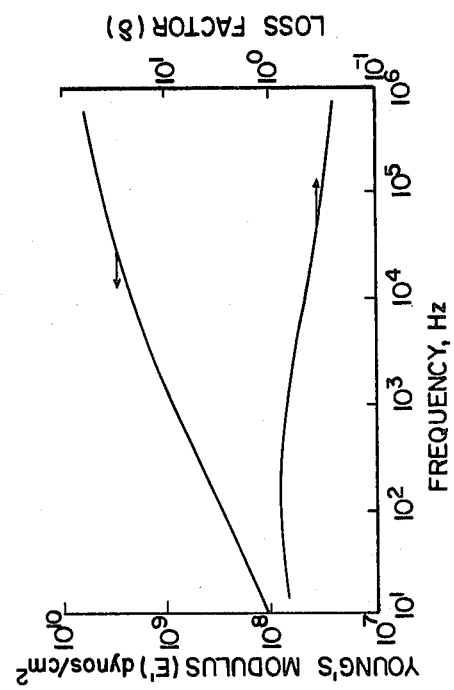

A typical plot of $(T-T_o)$ against $(T-T_o)/\log a_T$ for neoprene rubber is shown in FIG. 8. A least-square curve fit was applied on the data points. Since a good fit was obtained, there is confidence in the shifted modulus and loss curves. Scatter in the data points would means the modulus and loss curves are shifted incorrectly, either too much to the left or right. Values of $c_1$ and $c_2$ at a reference temperature of 20° C. are listed in Table I.

TABLE I

WLF shift constants for various rubber compounds at a reference temperature of 20° C.

|  | $c_1$ | $c_2$ |
|---|---|---|
| Polyurethane | 5.37 | 51 |
| Neoprene | 4.09 | 67 |
| Nitrile | 9.35 | 133 |

Three rubber compounds were selected for testing with the apparatus of the subject invention. The physical properties of the compounds are listed in Table II.

TABLE II

Physical Properties of various rubbers.

|  | Density (g/cm$^3$) | Shore A hardness |
|---|---|---|
| Polyurethane | 1.072 | 63 |
| Neoprene | 1.32 | 68 |
| Nitrile | 1.132 | 58 |

The polyurethane rubber, U.S. Polymerics V-356, was obtained commercially. The rubber was prepared in two steps: first, a hydroxy terminated, block copolymer of polyether is reacted with an excess amount of diisocyanate to yield a prepolymer; second, the prepolymer and the excess diisocyanate is cured with a mixture of diols and triols of low molecular weight to yield a crosslinked polyether polyurethane.

A commercially available neoprene (polychloroprene) rubber (MIL R 6855 C class 2) was selected because of its wide use.

A nitrile butadiene copolymer rubber gum stock, B. F. Goodrich Chemical Company Hycar 1034-60, was used to prepare a nitrile rubber using the recipe given in Table III.

TABLE III

Nitrile rubber recipe.

| Hycar 1034-60 (Goodrich) | 100 | pts |
|---|---|---|
| United N234 (Ashland) | 40 | pts |
| Dioctyl Phthalate (DOP) (Ashland) | 15 | pts |
| St. Joe 42-41 (Harwick) | 3 | pts |
| MBTS (American Cyanamid) | 1.5 | pts |
| Tire 21-12 Mc-TP Sulfur (Stauffer) | 1.5 | pts |
| Stearic Acid F-1000 (Harwick) | 1 | pt |
| AgeRite Stalite (Vanderbilt) | 1 | pt |
| Cure 30 min at 320° F. | 163 | pts |

Figure 3:
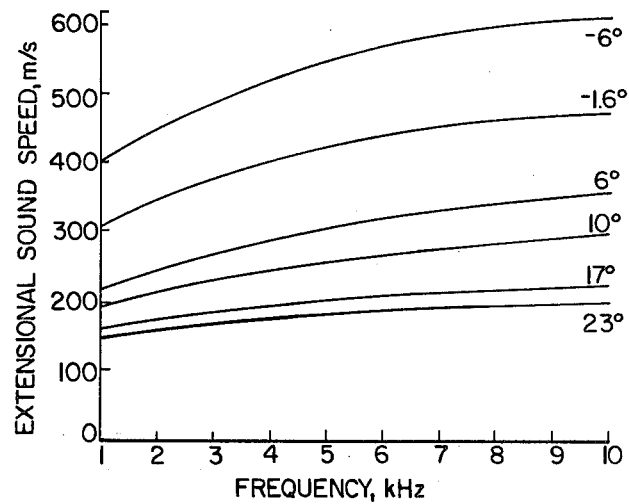
FIG. 3 illustrates extensional sound speed versus frequency for nitrile rubber at various temperatures.
Figure 4:
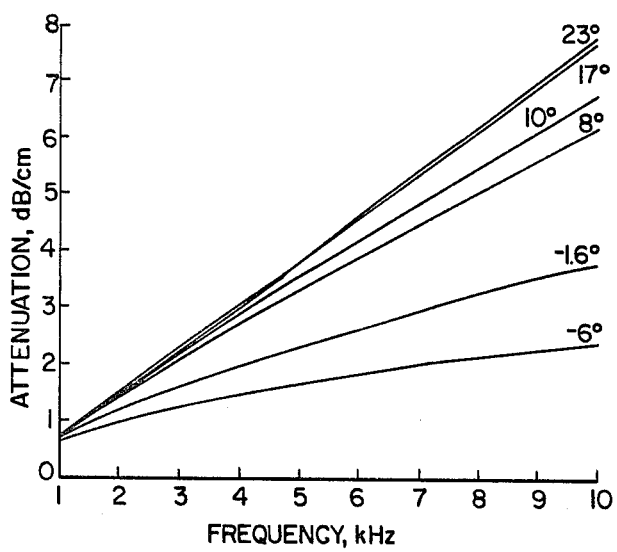
FIG. 4 illustrates attenuation versus frequency for nitrile rubber at various temperatures.

As a matter of convenience in shifting the data, measurements were made over the frequency range 1-10 kHz at various temperatures from 4° to 47° C. Typical plots of sound speed and attenuation versus frequency at various temperatures are presented in FIGS. 3 and 4 for nitrile rubber. The sound speed increases with increasing frequency and decreasing temperature, while the attenuation increases with increasing frequency and increasing temperature.

Figure 5:
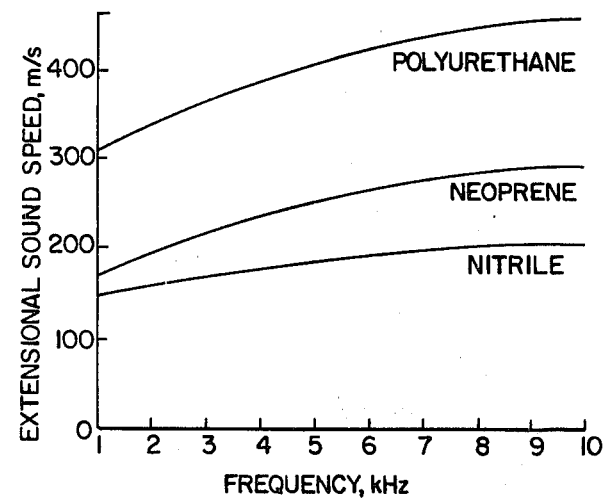
FIG. 5 illustrates extensional sound speed versus frequency for various rubber compounds.
Figure 6:
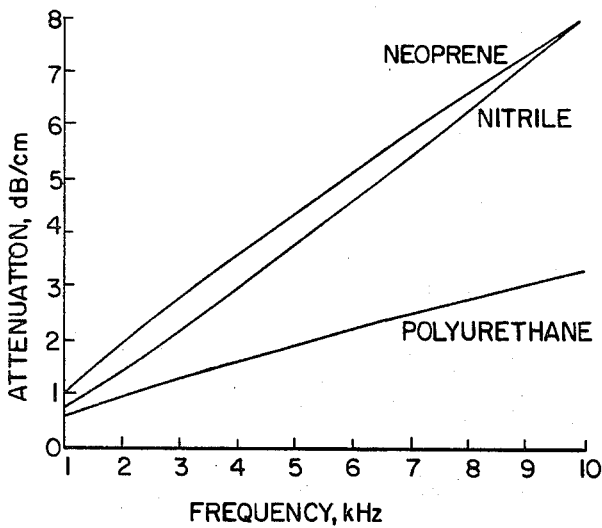
FIG. 6 illustrates attenuation versus frequency for various rubber compounds.

A comparison of sound speed and attenuation versus frequency at room temperature (20° C.) for the three rubber compounds is illustrated in FIGS. 5 and 6.

Figure 2:
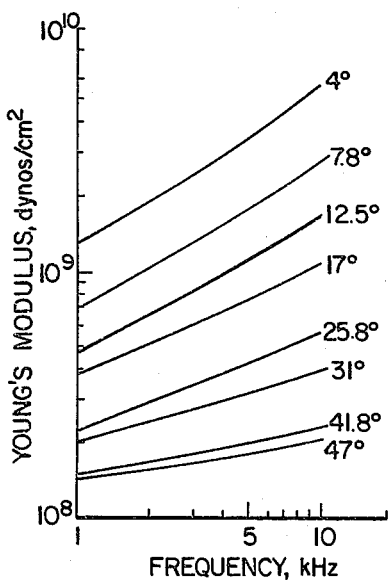
FIG. 2 illustrates Young's modulus versus frequency for neoprene rubber at various temperatures.
Figure 7:
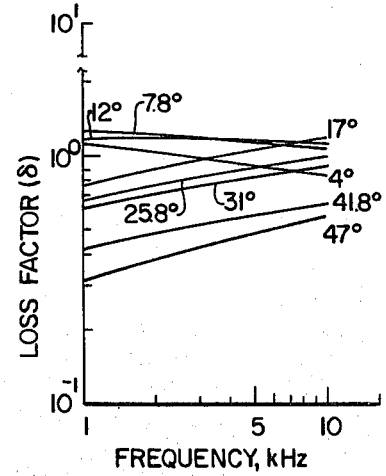
FIG. 7 illustrates loss factor versus frequency for neoprene rubber at various temperatures.

Typical plots of Young's modulus and loss factor versus frequency at various temperatures are shown in FIGS. 2 and 7 for neoprene rubber. The modulus increases with frequency and decreases with temperature. The loss also increases with frequency and decreases with temperature. However, at temperatures below 12°, the trend reverses.

It is apparent that the disclosed method and instrument provides for rapidly and reliably measuring the viscoelastic properties of rubber compounds over a wide frequency range. The instrument also provides a method for continuously measuring the viscoelastic properties of rubber compounds which minimizes measurement variations due to the surface roughness of the compound.

Many obvious modifications and embodiments of the specific invention, other than those set forth above, will readily come to mind to one skilled in the art having the benefit of the teachings presented in the foregoing description and the accompanying drawings of the subject invention and hence it is to be understood that such modifications are included within the scope of the appended claims.

What is claimed and desired to be secured by Letters Patent of the United States is:

1. An instrument for measuring the viscoelastic properties of rubber compounds, comprising:
    means generating an extensional acoustic wave in the rubber compound at one or more frequencies;
    means monitoring the rubber compound for deformation, said monitoring means being positioned at a first distance from the generating means; and
    means varying the distance between the generating means and the monitoring means, said varying means providing a second distance between the generating means and the monitoring means;
    whereby the generating means creates an extensional acoustic wave in the rubber compound which deforms the compound at the one or more frequencies, the monitoring means monitors the deformation of the compound at the one or more frequencies for amplitude and phase at the first distance relative to the phase of the wave at the generating means, the varying means provides for a second distance between the generating means and the monitoring means and the monitoring means monitors the deformation at the one or more frequencies for amplitude and phase at the second distance relative to the phase of the wave at the generating means.

2. The invention as in claim 1 wherein the one or more frequencies is a range of frequencies, said range being swept by the generating means.

3. The invention as in claims 1 or 2 wherein the generating means comprises:
    an electromechanical shaker;
    a frequency synthesizer which signal varies the frequency sweep of the shaker; and
    means controlling the synthesizer.

4. The invention as in claim 3 wherein the monitoring means comprises a piezoelectric transducer.

5. The invention as in claim 4 wherein the piezoelectric transducer is a phonograph cartridge.

6. The invention as in claim 4 wherein the monitoring means further comprises:
an amplifier amplying the transducer signal; and
a network analyzer receiving the amplified signal, said analyzer comparing the transducer signal to the frequency synthesizer signal.

7. The invention as in claim 6 wherein the monitoring means further comprises:
a plotter for plotting the viscoelastic properties; and
an oscilloscope for visually displaying the synthesizer signal and the transducer signal.

8. The invention as in claim 3 wherein the viscoelastic properties are Young's modulus and loss factor.

9. The invention as in claim 6 wherein the means controlling the synthesizer comprises a computer controlling the sweep of the frequency synthesizer, storing output of the network analyzer, and converting amplitude and relative phase of the deformation into the viscoelastic properties of the rubber compound.

10. The invention as in claim 6 wherein the signal from the synthesizer is filtered to provide a constant output level to the network analyzer at low frequencies.

11. The invention as in claim 6 wherein the frequency range is from 100 Hz to 40 KHz.

12. The invention as in claim 6 wherein the generating means and monitoring means are mounted in a refrigerator oven.

13. The invention as in claim 6 wherein the varying means comprise spacers which vary the distance between the generating means and the monitoring means.

14. A method for determining the viscoelastic properties of a rubber compound, comprising:

generating an extensional acoustic wave in the compound at one or more frequencies by means of a wave generator;
monitoring the deformation of the compound for values of amplitude and phase relative to the phase of the wave at the wave generator at one or more frequencies at a first distance from the wave generator;
monitoring the deformation of the compound for values of amplitude and phase relative to the phase of the wave at the wave generator at one or more frequencies at a second distance from the wave generator; and
converting the values for amplitude and relative phase obtained by monitoring the compound at the first and second distances into the viscoelastic properties of the rubber compound.

15. The method as in claim 14 wherein the wave generator is an electromechanical shaker and the deformation of the compound is measured with a piezoelectric transducer.

16. The method as in claim 15 wherein the one or more frequencies is a range of frequencies.

17. The method as in claim 16 wherein the frequency synthesizer sweeps the shaker through the frequency range and a network analyzer compares the signals from the transducer and the synthesizer.

18. The method as in claim 17 wherein a computer controls the sweep of the synthesizer, stores the data from the network analyzer and converts the amplitude and relative phase into the viscoelastic properties of the compound.

19. The invention as in claims 1 or 14 wherein the rubber compound is in the form of an elongated strip.

* * * * *